US009901753B2

(12) United States Patent
Cain et al.

(10) Patent No.: US 9,901,753 B2
(45) Date of Patent: Feb. 27, 2018

(54) ULTRASOUND LITHOTRIPSY AND HISTOTRIPSY FOR USING CONTROLLED BUBBLE CLOUD CAVITATION IN FRACTIONATING URINARY STONES

(75) Inventors: Charles A. Cain, Ann Arbor, MI (US); Timothy L. Hall, Ann Arbor, MI (US); William W. Roberts, Saline, MI (US); Zhen Xu, Ann Arbor, MI (US); J. Brian Fowlkes, Ann Arbor, MI (US); Thomas W. Davison, Naples, FL (US)

(73) Assignees: THE REGENTS OF THE UNIVERSITY OF MICHIGAN, Ann Arbor, MI (US); HISTOSONICS, INC., Ann Arbor, MI (US)

( * ) Notice: Subject to any disclaimer, the term of this patent is extended or adjusted under 35 U.S.C. 154(b) by 1753 days.

(21) Appl. No.: 12/868,775

(22) Filed: Aug. 26, 2010

(65) Prior Publication Data
US 2011/0054363 A1 Mar. 3, 2011

Related U.S. Application Data

(60) Provisional application No. 61/237,011, filed on Aug. 26, 2009.

(51) Int. Cl.
*A61N 7/00* (2006.01)
*A61B 17/225* (2006.01)
(Continued)

(52) U.S. Cl.
CPC ............... *A61N 7/00* (2013.01); *A61B 8/00* (2013.01); *A61B 17/225* (2013.01);
(Continued)

(58) Field of Classification Search
USPC ........................................................ 600/427
See application file for complete search history.

(56) References Cited

U.S. PATENT DOCUMENTS 3,243,497 A   3/1966 Kendall et al.
3,679,021 A   7/1972 Goldberg et al.
(Continued)

FOREIGN PATENT DOCUMENTS

CN   102481164 A   5/2012
DE   3220751 A1   12/1983
(Continued)

OTHER PUBLICATIONS

Pishchalnikov et al. (Cavitation Bubble Cluster Activity in the Breakage of Kidney Stones by Lithotripter Shock Waves, J Endourol. Sep. 2003 ; 17(7): 435-446.).*

(Continued)

*Primary Examiner* — Serkan Akar
(74) *Attorney, Agent, or Firm* — Shay Glenn LLP

(57) ABSTRACT

A medical imaging and therapy device is provided that may include any of a number of features. One feature of the device is that it can deliver Lithotripsy therapy to a patient, so as to fractionate urinary stones. Another feature of the device is that it can deliver Histotripsy therapy to a patient, so as to erode urinary stones. In some embodiments, the medical imaging and therapy device is configured to target and track urinary stones in the patient during therapy. Methods associated with use of the medical imaging and therapy device are also covered.

12 Claims, 4 Drawing Sheets

(51) Int. Cl.
  *A61B 8/00* (2006.01)
  *A61B 17/00* (2006.01)
  *A61B 17/22* (2006.01)
  *A61B 90/00* (2016.01)

(52) U.S. Cl.
  CPC . *A61B 17/2256* (2013.01); *A61B 2017/00172* (2013.01); *A61B 2017/22008* (2013.01); *A61B 2090/378* (2016.02)

(56) References Cited

U.S. PATENT DOCUMENTS

| | | | |
|---|---|---|---|
| 4,016,749 A | 4/1977 | Wachter |
| 4,024,501 A | 5/1977 | Herring et al. |
| 4,051,394 A | 9/1977 | Tieden |
| 4,117,446 A | 9/1978 | Alais |
| 4,269,174 A | 5/1981 | Adair |
| 4,277,367 A | 7/1981 | Madsen et al. |
| 4,351,038 A | 9/1982 | Alais |
| 4,406,153 A | 9/1983 | Ophir et al. |
| 4,440,025 A | 4/1984 | Hayakawa et al. |
| 4,453,408 A | 6/1984 | Clayman |
| 4,483,345 A | 11/1984 | Miwa |
| 4,549,533 A | 10/1985 | Cain et al. |
| 4,550,606 A | 11/1985 | Drost |
| 4,575,330 A | 3/1986 | Hull |
| 4,622,972 A | 11/1986 | Giebeler, Jr. |
| 4,625,731 A | 12/1986 | Quedens et al. |
| 4,641,378 A | 2/1987 | McConnell et al. |
| 4,669,483 A | 6/1987 | Hepp et al. |
| 4,689,986 A | 9/1987 | Carson et al. |
| 4,757,820 A | 7/1988 | Itoh |
| 4,791,915 A | 12/1988 | Barsotti et al. |
| 4,819,621 A | 4/1989 | Ueberle et al. |
| 4,829,491 A | 5/1989 | Saugeon et al. |
| 4,856,107 A | 8/1989 | Dory |
| 4,865,042 A | 9/1989 | Umemura et al. |
| 4,888,746 A | 12/1989 | Wurster et al. |
| 4,890,267 A | 12/1989 | Rudolph |
| 4,922,917 A | 5/1990 | Dory |
| 4,938,217 A | 7/1990 | Lele |
| 4,957,099 A | 9/1990 | Hassler |
| 4,973,980 A | 11/1990 | Howkins et al. |
| 4,984,575 A | 1/1991 | Uchiyama et al. |
| 4,991,151 A | 2/1991 | Dory |
| 4,995,012 A | 2/1991 | Dory |
| RE33,590 E | 5/1991 | Dory |
| 5,014,686 A | 5/1991 | Schafer |
| 5,065,751 A | 11/1991 | Wolf |
| 5,080,101 A | 1/1992 | Dory |
| 5,080,102 A | 1/1992 | Dory |
| 5,091,893 A | 2/1992 | Smith et al. |
| 5,092,336 A | 3/1992 | Fink |
| 5,097,709 A | 3/1992 | Masuzawa et al. |
| 5,111,822 A | 5/1992 | Dory |
| 5,143,073 A | 9/1992 | Dory |
| 5,143,074 A | 9/1992 | Dory |
| 5,150,711 A | 9/1992 | Dory |
| 5,158,070 A | 10/1992 | Dory |
| 5,158,071 A | 10/1992 | Umemura et al. |
| 5,163,421 A | 11/1992 | Bernstein et al. |
| 5,165,412 A | 11/1992 | Okazaki |
| 5,174,294 A | 12/1992 | Saito |
| 5,209,221 A | 5/1993 | Riedlinger |
| 5,215,680 A | 6/1993 | D'Arrigo |
| 5,219,401 A | 6/1993 | Cathignol et al. |
| 5,230,340 A | 7/1993 | Rhyne |
| 5,295,484 A | 3/1994 | Marcus et al. |
| 5,316,000 A | 5/1994 | Chapelon et al. |
| 5,354,258 A | 10/1994 | Dory |
| 5,380,411 A | 1/1995 | Schlief |
| 5,409,002 A | 4/1995 | Pell |
| 5,431,621 A | 7/1995 | Dory |
| 5,435,311 A | 7/1995 | Umemura et al. |
| 5,443,069 A | 8/1995 | Schaetzle |
| 5,469,852 A | 11/1995 | Nakamura et al. |
| 5,474,071 A | 12/1995 | Chapelon et al. |
| 5,474,531 A | 12/1995 | Carter |
| 5,501,655 A | 3/1996 | Rolt et al. |
| 5,520,188 A | 5/1996 | Hennige et al. |
| 5,523,058 A | 6/1996 | Umemura et al. |
| 5,524,620 A | 6/1996 | Rosenschein |
| 5,540,909 A | 7/1996 | Schutt |
| 5,542,935 A | 8/1996 | Unger et al. |
| 5,558,092 A | 9/1996 | Unger et al. |
| 5,563,346 A | 10/1996 | Bartelt et al. |
| 5,566,675 A | 10/1996 | Li et al. |
| 5,573,497 A | 11/1996 | Chapelon |
| 5,580,575 A | 12/1996 | Unger et al. |
| 5,582,578 A | 12/1996 | Zhong et al. |
| 5,590,657 A | 1/1997 | Cain et al. |
| 5,601,526 A | 2/1997 | Chapelon et al. |
| 5,617,862 A | 4/1997 | Cole et al. |
| 5,648,098 A | 7/1997 | Porter |
| 5,666,954 A | 9/1997 | Chapelon et al. |
| 5,676,452 A | 10/1997 | Scholz |
| 5,676,692 A | 10/1997 | Sanghvi et al. |
| 5,678,554 A | 10/1997 | Hossack et al. |
| 5,694,936 A | 12/1997 | Fujimoto et al. |
| 5,695,460 A | 12/1997 | Siegel et al. |
| 5,717,657 A | 2/1998 | Ruffa |
| 5,724,972 A | 3/1998 | Petrofsky |
| 5,743,863 A | 4/1998 | Chapelon |
| 5,753,929 A | 5/1998 | Bliss |
| 5,759,162 A | 6/1998 | Oppelt et al. |
| 5,766,138 A | 6/1998 | Rattner |
| 5,769,790 A | 6/1998 | Watkins et al. |
| 5,797,848 A | 8/1998 | Marian et al. |
| 5,823,962 A | 10/1998 | Schaetzle et al. |
| 5,827,204 A * | 10/1998 | Grandia et al. .......... 601/2 |
| 5,836,896 A | 11/1998 | Rosenschein |
| 5,849,727 A | 12/1998 | Porter et al. |
| 5,873,902 A | 2/1999 | Sanghvi et al. |
| 5,879,314 A | 3/1999 | Peterson et al. |
| 5,932,807 A | 8/1999 | Mallart |
| 5,947,904 A | 9/1999 | Hossack et al. |
| 6,001,069 A | 12/1999 | Tachibana et al. |
| 6,022,309 A | 2/2000 | Celliers et al. |
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,308,585 B1 | 10/2001 | Nilsson et al. |
| 6,308,710 B1 | 10/2001 | Silva |
| 6,309,355 B1 | 10/2001 | Cain et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |

(56) References Cited

U.S. PATENT DOCUMENTS

| | | |
|---|---|---|
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 8,333,115 B1 | 12/2012 | Garvey et al. |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0181833 A1 | 9/2003 | Faragalla et al. |
| 2003/0199857 A1* | 10/2003 | Eizenhofer .............. 606/2.5 |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0236248 A1 | 11/2004 | Svedman |
| 2004/0243021 A1 | 12/2004 | Murphy et al. |
| 2005/0038339 A1 | 2/2005 | Chauhan et al. |
| 2005/0038361 A1* | 2/2005 | Zhong et al. .............. 601/4 |
| 2005/0152561 A1 | 7/2005 | Spencer |
| 2005/0154314 A1 | 7/2005 | Quistgaard |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1* | 10/2006 | Sinelnikov et al. .............. 601/2 |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0161902 A1* | 7/2007 | Dan .............................. 600/458 |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319356 A1 | 12/2008 | Cain et al. |
| 2008/0319376 A1 | 12/2008 | Wilcox et al. |
| 2009/0030339 A1 | 1/2009 | Cheng et al. |
| 2009/0112098 A1 | 4/2009 | Vaezy et al. |
| 2009/0177085 A1 | 7/2009 | Maxwell et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2010/0011845 A1 | 1/2010 | Laugharn et al. |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0305432 A1 | 12/2010 | Duhay et al. |
| 2010/0317971 A1 | 12/2010 | Fan et al. |
| 2011/0040190 A1 | 2/2011 | Jahnke et al. |
| 2011/0112400 A1 | 5/2011 | Emery et al. |
| 2011/0118602 A1 | 5/2011 | Weng et al. |
| 2011/0172529 A1 | 7/2011 | Gertner |
| 2011/0178444 A1 | 7/2011 | Slayton et al. |
| 2011/0251528 A1 | 10/2011 | Canney et al. |
| 2011/0257524 A1 | 10/2011 | Gertner |
| 2011/0263967 A1 | 10/2011 | Bailey et al. |
| 2012/0010541 A1 | 1/2012 | Cain et al. |
| 2012/0029353 A1 | 2/2012 | Slayton et al. |
| 2012/0059264 A1 | 3/2012 | Hope Simpson et al. |
| 2012/0092724 A1 | 4/2012 | Pettis |
| 2012/0130288 A1 | 5/2012 | Holland et al. |
| 2012/0172720 A1 | 7/2012 | Kawabata |
| 2012/0189998 A1 | 7/2012 | Kruecker et al. |
| 2012/0271223 A1 | 10/2012 | Khanna |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0190623 A1 | 7/2013 | Bertolina et al. |
| 2013/0289593 A1 | 10/2013 | Hall et al. |
| 2013/0303906 A1 | 11/2013 | Cain et al. |
| 2014/0073995 A1 | 3/2014 | Teofilovic et al. |

FOREIGN PATENT DOCUMENTS

| | | |
|---|---|---|
| DE | 3544628 A1 | 6/1987 |
| DE | 3817094 A1 | 11/1989 |
| DE | 4012760 A1 | 5/1992 |
| EP | 0017382 A1 | 10/1980 |
| EP | 0320303 A2 | 6/1989 |
| EP | 0332871 A2 | 9/1989 |
| EP | 0384831 A2 | 8/1990 |

(56) References Cited

FOREIGN PATENT DOCUMENTS

| | | |
|---|---|---|
| EP | 0755653 A1 | 1/1997 |
| EP | 1374785 A1 | 1/2004 |
| EP | 1504713 A1 | 2/2005 |
| EP | 2397188 A1 | 12/2011 |
| GB | 2099582 A | 12/1982 |
| JP | 60-80779 A | 5/1985 |
| JP | HEI 60-80779 A | 5/1985 |
| JP | 61-196718 A | 8/1986 |
| JP | HEI 2-215451 | 8/1990 |
| JP | HEI 7-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | HEI 10-512477 | 12/1998 |
| JP | 2000300559 A | 10/2000 |
| JP | 2003-510159 A | 3/2003 |
| JP | 2004-505660 A | 2/2004 |
| JP | 2005167058 A | 6/2005 |
| JP | 2007520307 A | 7/2007 |
| JP | 2010019554 A | 1/2010 |
| JP | 2010029650 A | 2/2010 |
| JP | 2010204068 A | 9/2010 |
| JP | 2004-512502 A | 4/2014 |
| WO | WO94/06355 A1 | 3/1994 |
| WO | WO 02/32506 A1 | 4/2002 |
| WO | WO2005/018469 A1 | 3/2005 |
| WO | WO 2007/038160 * | 4/2007 ............ A61B 8/00 |
| WO | WO 2008/051484 A2 | 5/2008 |
| WO | WO2011/040054 A1 | 7/2011 |
| WO | WO 2011/092683 A1 | 8/2011 |
| WO | WO2011/154654 A2 | 12/2011 |

OTHER PUBLICATIONS

Sapozhnikov et al. (Ultrasound-Guided Localized Detection of Cavitation During Lithotripsy in Pig Kidney In Vivo, 2001 IEEE Ultrasonics Symposium-1348).*
Cain, Charles A.; Histrotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Parsons et al.; Pulsed cavitational ultrasound therapy for controlled tissue homogenization; Ultrasound in Med. & Biol.; vol. 32; pp. 115-129; 2006.
Roberts et al.; Pulsed cavitational ultrasound: a noninvasive technology for controlled tissue ablation (histotripsy) in the rabbit kidney; Journal of Urology; vol. 175; pp. 734-738; 2006.
Xu et al.; A new strategy to enhance cavitational tissue erosion by using a high intensity initiating sequence; IEEE Trans Ultrasonics Ferroelectrics and Freq Control; vol. 53; pp. 1412-1424; 2006.
Xu et al.; Controlled ultrasound tissue erosion: the role of dynamic interaction between insonation and microbubble activity; Journal of the Acoustical Society of America; vol. 117; pp. 424-435; 2005.
Xu et al.; Controlled ultrasound tissue erosion; IEEE Transaction on Ultrasonics, Ferroelectrics, and Frequency Control; vol. 51; pp. 726-736; 2004.
Xu et al.; Effects of acoustic parameters on bubble cloud dynamics in ultrasound tissue erosion (histotripsy); Journal of the Acoustical Society of America; vol. 122; pp. 229-236; 2007.
Xu et al.; High Speed Imaging of Bubble Clouds Generated in Pulsed Ultrasound Cavitational Therapy'Histotripsy; IEEE Trans Ultrason Ferroelectr Freq Control; ; vol. 54; No. 10; pp. 2091R2101; Oct. 2007.
Xu et al.; Investigation of intensity threshold for ultrasound tissue erosion; Ultrasound in Med. & Biol.; vol. 31; pp. 1673-1682; 2005.
Xu et al.; Optical and acoustic monitoring of bubble cloud dynamics at a tissue-fluid interface in ultrasound tissue erosion; Journal of the Acoustical Society of America; vol. 121; pp. 2421-2430; 2007.

Hall et al.; U.S. Appl. No. 12/868,768 entitled "Micromanipulator Control Arm for Therapeutic and Imaging Ultrasound Transducers," filed Aug. 26, 2010.
Cain et al.; U.S. Appl. No. 12/887,705 entitled "Gel phantoms for testing cavitational ultrasound (histotripsy) transducers," filed Sep. 22, 2010.
Hall et al.; Imaging feedback of tissue liquefaction (histotripsy) in ultrasound surgery; IEEE Ultrasonic Symposium, Sep. 18-25, 2005, pp. 1732-1734.
Appel et al.; Stereoscopic highspeed recording of bubble filaments; Ultrasonics Sonochemistry; vol. 11(1); pp. 39-42; Jan. 2004.
Atchley et al.; Thresholds for cavitation produced in water by pulsed ultrasound; Ultrasonics.; vol. 26(5); pp. 280-285; Sep. 1988.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43 (10); pp. 3113-3128; Oct. 1998.
Lauterborn et al.; Cavitation bubble dynamics studied by high speed photography and holography: part one; Ultrasonics; vol. 23; pp. 260-268; Nov. 1985.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.
Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.
Porter et al.; Reduction in left ventricular cavitary attenuation and improvement in posterior myocardial contrast . . . ; J Am Soc Echocardiography; pp. 437-441; Jul.-Aug. 1996.
Roy et al.; A precise technique for the measurement of acoustic cavitation thresholds and some preliminary results; Journal of the Acoustical Society of America; vol. 78(5); pp. 1799-805; Nov. 1985.
Sokolov et al.; Use of a dual-pulse lithotripter to generate a localized and intensified cavitation field; Journal of the Acoustical Society of America; vol. 110(3); pp. 1685-1695; Sep. 2001.
Teofilovic, Dejan; U.S. Appl. No. 13/446,783 entitled "Systems and Methods for Obtaining Large Creepage Isolation on Printed Circuit Boards," filed Apr. 13, 2012.
Cain, Charles A.; U.S. Appl. No. 13/570,708 entitled "Lesion Generation Through Bone Using Histotripsy Therapy Without Aberration Correction," filed Aug. 9, 2012.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Emelianov et al.; Triplex ultrasound: Elasticity imaging to age deep venous thrombosis; Ultrasound Med Biol; 28(6); pp. 757-767; Jun. 2002.
Hynynen et al.; Tissue thermometry during ultrasound exposure; European Urology; 23(Suppl 1); pp. 12-16; 1993 (year of pub. sufficiently earlier than effective US filing date and any foreign priority date).
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.

(56) References Cited

OTHER PUBLICATIONS

Konofagou; Quo vadis elasticity imaging?; Ultrasonics; 42(1-9); pp. 331-336; Apr. 2004.
Kruse et al.; Tissue characterization using magnetic resonance elastography: Preliminary results; Phys. Med. Biol; 45(6); pp. 1579-1590; Jun. 2000.
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Nightingale et al.; Analysis of contrast in images generated with transient acoustic radiation force; Ultrasound Med Biol; 32(1); pp. 61-72; Jan. 2006.
Okada et al.; A case of hepatocellular carcinoma treated by MR-guided focused ultrasound ablation with respiratory gating; Magn Reson Med Sci; 5(3); pp. 167-171; Oct. 2006.
Rowland et al.; MRI study of hepatic tumours following high intensity focused ultrasound surgery; British Journal of Radiology; 70; pp. 144-153; Feb. 1997.
Sapareto et al.; Thermal dose determination in cancer therapy; Int J Radiat Oncol Biol Phys; 10(6); pp. 787-800; Apr. 1984.
Souchon et al.; Visualisation of HIFU lesions using elastography of the human prostate in vivo: Preliminary results; Ultrasound Med. Biol; 29(7); pp. 1007-1015; Jul. 2003.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).
Zheng et al.; An acoustic backscatter-based method for localization of lesions induced by high-intensity focused ultrasound; Ultrasound Med Biol; 36(4); pp. 610-622; Apr. 2010.
Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
AVOGO Technologies; ACNV2601 High Insulation Voltage 10 MBd Digital Opotcoupler. Avago Technologies Data Sheet; pp. 1-11; Jul. 29, 2010.
Bjoerk et al.; Cool/MOS CP—How to make most beneficial use of the generation of super junction technology devices. Infineon Technologies AG. Feb. 2007 [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c900048&fileId=db3a304412b407950112b40ac9a40688>pp. 1, 4, 14.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clement et al.; A hemisphere array for non-invasive ultrasound brain therapy and surgery; Physics in Medicine and Biology, vol. 45, p. 3707-3719, Dec. 2000.
Desilets et al.; The Design of Efficient Broad-Band Piezoelectric Transducers; Sonics and Ultrasonics, IEEE Transactions on, vol. 25, pp. 115-125, May 1978.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; Aip Conference Proceedings, Boston, MA; vol. 829, pp. 445-449, Oct. 27-29, 2005.
Hall et al.; Histotripsy of the prostate: dose effects in a chronic canine model; Urology; 74(4); pp. 932-937; Oct. 2009 (author manuscript).
Hartmann; Ultrasonic properties of poly(4-methyl pentene-1), Journal of Applied Physics, vol. 51, pp. 310-314, Jan. 1980.
Kim et al.; Dependence of particle volume fraction on sound velocity and attenuation of EPDM composites; Ultrasonics, vol. 46, pp. 177-183, Feb. 2007.
Krimholtz et al.; New equivalent circuits for elementary piezoelectric transducers; Electronics Letters, vol. 6, pp. 398-399, Jun. 1970.
Lake et al.; Histotripsy: minimally invasive technology for prostatic tissue ablation in an in vivo canine model; Urology; 72(3); pp. 682-686; Sep. 2008.
Lensing et al.; Deep-vein thrombosis; The Lancet, vol. 353, pp. 479-485, Feb. 6, 1999.
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Rosenschein et al.; Ultrasound Imaging-Guided Noninvasive Ultrasound Thrombolysis: Preclinical Results; Circulation; vol. 102; pp. 238-245, Jul. 11, 2000.
Sato et al.; Experimental Investigation of Phased Array Using Tapered Matching Layers. 2002 IEEE Ultrasound Symposium. vol. 2; pp. 1235-1238, Oct. 2002.
Simonin et al.; Characterization of heterogeneous structure in a polymer object manufactured by stereolithography with low-frequency microechography; Journal of Materials Chemistry; vol. 6, pp. 1595-99, Sep. 1996.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument).
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009 (author manuscript).
Yan et al.; A review of rapid prototyping technologies and systems; Computer-Aided Design, vol. 28, pp. 307-318, Apr. 1996.

(56) References Cited

OTHER PUBLICATIONS

Xu et al.; U.S. Appl. No. 14/046,024 entitled "Bubble-induced color doppler feedback during histotripsy," filed Oct. 4, 2013.
AVTECH; AVR-8 Data sheet; May 23, 2004; 3 pages; retrieved from the internet (http//www.avtechpulse.com).
Hobarth et al.; Color flow doppler sonography for extracorporal shock wave lithotripsy; Journal of Urology; 150(6); pp. 1768-1770; Dec. 1, 1993.
Maxwell et al.; In-vivo study of non-invasive thrombolysis by histotripsy in a porcine model; IEEE international Ultrasonics Symposium; IEEE; p. 220-223; Sep. 20, 2009.
Avago Technologies; Avago's ACNV2601 optocoupler is an optically coupled logic gate; Data Sheet; 2 pages; Jul. 29, 2010.

\* cited by examiner

ULTRASOUND LITHOTRIPSY AND HISTOTRIPSY FOR USING CONTROLLED BUBBLE CLOUD CAVITATION IN FRACTIONATING URINARY STONES

CROSS REFERENCE TO RELATED APPLICATIONS

This application claims the benefit under 35 U.S.C. 119 of U.S. Provisional Patent Application No. 61/237,011, filed Aug. 26, 2009, titled "Devices and Methods for Using Controlled Bubble Cloud Cavitation in Fractionating Kidney Stones". This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention generally relates to ultrasound treatment of urinary stones. More specifically, the present invention relates to using a combination of Lithotripsy and Histotripsy to fractionate and erode urinary stones.

BACKGROUND OF THE INVENTION

Histotripsy and Lithotripsy are non-invasive tissue ablation modalities that focus pulsed ultrasound from outside the body to a target tissue inside the body. Histotripsy mechanically damages tissue through cavitation of microbubbles, and Lithotripsy is typically used to fragment urinary stones with acoustic shockwaves.

Histotripsy is the mechanical disruption via acoustic cavitation of a target tissue volume or tissue embedded inclusion as part of a surgical or other therapeutic procedure. Histotripsy works best when a whole set of acoustic and transducer scan parameters controlling the spatial extent of periodic cavitation events are within a rather narrow range. Small changes in any of the parameters can result in discontinuation of the ongoing process.

Histotripsy requires high peak intensity acoustic pulses which in turn require large surface area focused transducers. These transducers are often very similar to the transducers used for Lithotripsy and often operate in the same frequency range. The primary difference is in how the devices are driven electrically.

As shown by FIGS. 1A-1B, Histotripsy pulses comprise (usually) small number of cycles of a sinusoidal driving voltage whereas Lithotripsy is (most usually) driven by a single high voltage pulse with the transducer responding at its natural frequencies. Even though the Lithotripsy pulse is only one cycle, its negative pressure phase length is equal to or greater than the entire length of the Histotripsy pulse, lasting tens of microseconds. This negative pressure phase allows generation and continual growth of the bubbles, resulting in bubbles of sizes up to 1 mm. The Lithotripsy pulses use the mechanical stress produced by a shockwave and these 1 mm bubbles to fracture the stones into smaller pieces.

In comparison, each negative and positive cycle of a Histotripsy pulse grows and collapses the bubbles, and the next cycle repeats the same process. The maximal sizes of bubbles reach approximately tens to hundreds of microns. These micron size bubbles interact with a tissue surface to mechanically damage tissue.

In addition, Histotripsy delivers hundreds to thousands of pulses per second, i.e., 100-1 kHz pulse repetition frequency. Lithotripsy only works well within a narrow range of pulse repetition frequency (usually 0.5-2 Hz, which is the current limit in the United States and in Europe, however higher limits up to 4-5 Hz are contemplated). Studies show that the efficacy and efficiency of Lithotripsy decreases significantly when the pulse repetition frequency is increased to 10-100 Hz. The reduced efficiency is likely due to the increased number of mm size bubbles blocking the shock waves and other energy from reaching the stone.

Prior art treatment of nephrolithiasis (urinary stones) included early generation hydroelectric spark gap Lithotripters, such as the Donier HM3, which targeted a large treatment area, covering a sizeable portion of the kidney. For this reason, treatment success rates were high without the need for precise image guidance, yet substantial damage to the kidney tissue within the large focal volume also occurred. Subsequent Lithotripter development was focused on reducing renal injury by decreasing the focal volume. Some of the current third generation Lithotripters use piezoelectric (PZT) transducers, such as the Richard Wolf Piezolith 3000. The PZT transducer focused ultrasound in a small treatment region. Fluoroscope and ultrasound imaging can be utilized to target the urinary stones prior to and during treatment. By virtue of the smaller focus, the newer generation Lithotripters have reduced collateral tissue damage, but at the expense of success rates. Inaccuracies of targeting and respiratory motion of the kidneys decrease the fraction of pulses that directly impact the targeted stone.

Histotripsy also uses focused PZT transducers but has a different driving system. It uses ultrasound imaging to target the focused ultrasound to the stone and monitor the treatment in real time. The bubble clouds generated by Histotripsy show as a temporally changing hyperechoic zone on ultrasound images. The real-time guidance makes it possible to track the stone movement and adjust the focus position, thus further reducing possible collateral tissue damage. As described earlier, stone fragments produced by lithotripter vary from small granules less than 1.0 mm diameter to macroscopic fragments with diameters significantly greater than 1 mm (as shown in FIG. 2A), while Histotripsy erodes stones into fine particles smaller than 100 µm (as shown in FIG. 2B). Table 1 lists the Histotripsy and Lithotripsy parameters for comparison.

TABLE 1

Histotripsy and Lithotripsy Parameters

| Parameters | Histotripsy | Lithotripsy |
| --- | --- | --- |
| Energy Source | Short ultrasound pulses | Short ultrasound pulses |
| Image Guidance | Ultrasound | Fluoroscopy, Ultrasound |
| Peak negative pressure | ~8-40 MPa | ~10-25 MPa |
| Peak positive pressure | ~30-200 MPa | ~50-200 MPa |
| Pulse Length | 3-20 cycles | 1 cycle |
| Duty Cycle | ≤5% | <0.1% |
| Pulse Repetition Frequency | ≤5 kHz | ≤2 Hz |

Shockwave Lithotripsy is favorable in that it is a short (~30 minute) outpatient procedure that requires only IV sedation in the vast majority of patients. Post-operative pain generally resolves within 1-2 days. Ureteroscopy and percutaneous nephrolithotomy generally require general anesthesia. Although ureteroscopy is an outpatient procedure, patients often suffer with pain and discomfort from a ureteral stent for 4-7 days after treatment. Disadvantages of Lithotripsy include a stone free rate of ~65% percent 4 weeks after treatment (compared with 90-95% stone free rate in patients having percutaneous and ureteroscopic procedures) and the necessity and occasionally discomfort of passing stone fragments following treatment. Furthermore, urinary stones fragmented using shockwave Lithotripsy can remain up to several mm in size and include sharp or jagged edges that make them difficult and painful to pass through the urinary tract.

SUMMARY OF THE INVENTION

In some embodiments, a Lithotripsy-Histotripsy system is provided comprising a first therapy transducer configured to deliver Lithotripsy therapy to a target, a second therapy transducer configured to deliver Histotripsy therapy to the target, and a control system configured to switch between delivering Lithotripsy therapy from the first therapy transducer to delivering Histotripsy therapy from the second therapy transducer.

In some embodiments, the first therapy transducer is configured to apply acoustic pulses that operate at a frequency between approximately 50 KHz and 5 MHz, having a pulse intensity with a peak negative pressure of approximately 10-25 MPa, a peak positive pressure of more than 10 MPa, a pulse length of 1 cycle, a duty cycle less than 0.1%, and a pulse repetition frequency of less than 2 Hz.

In other embodiments, the second therapy transducer is configured to apply acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle of less than 5%, and a pulse repetition frequency of less than 5 KHz.

In some embodiments, the Lithotripsy-Histotripsy system further comprises an imaging system. In some embodiments, the imaging system comprises a fluoroscopic imaging system. In other embodiments, the imaging system comprises an ultrasound imaging system. In additional embodiments, the imaging system comprises a combination fluoroscopic and ultrasound imaging system. The imaging system can be configured to target and track a urinary stone in a patient.

In another embodiment of a Lithotripsy-Histotripsy system, the system comprises a multi-mode therapy transducer configured to deliver Lithotripsy therapy and Histotripsy therapy to a target, and a control system configured to switch between delivering Lithotripsy therapy from the multi-mode therapy transducer to delivering Histotripsy therapy from the multi-mode therapy transducer.

In some embodiments, the multi-mode therapy transducer is configured to apply acoustic pulses that operate at a frequency between approximately 50 KHz and 5 MHz, having a pulse intensity with a peak negative pressure of approximately 10-25 MPa, a peak positive pressure of more than 10 MPa, a pulse length of 1 cycle, a duty cycle less than 0.1%, and a pulse repetition frequency of less than 2 Hz, so as to deliver Lithotripsy therapy to the target.

In other embodiments, the multi-mode therapy transducer is configured to apply acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle of less than 5%, and a pulse repetition frequency of less than 5 KHz, so as to deliver Histotripsy therapy to the target.

In some embodiments, the Lithotripsy-Histotripsy system further comprises an imaging system. In some embodiments, the imaging system comprises a fluoroscopic imaging system. In other embodiments, the imaging system comprises an ultrasound imaging system. In additional embodiments, the imaging system comprises a combination fluoroscopic and ultrasound imaging system. The imaging system can be configured to target and track a urinary stone in a patient.

A method of treating urinary stones is also provided, comprising applying Histotripsy therapy to generate a bubble cloud, positioning the bubble cloud on a urinary stone, applying Lithotripsy therapy to generate a shock wave to fractionate the urinary stone into macroscopic urinary stone particles, and applying Histotripsy therapy to the macroscopic urinary stone particles to erode the macroscopic urinary stone particles.

In some embodiments, the positioning step further comprises positioning the bubble cloud on a urinary stone under imaging guidance. In other embodiments, the positioning step further comprises positioning the bubble cloud on a urinary stone under ultrasound imaging guidance. In additional steps, the positioning step further comprises positioning the bubble cloud on a urinary stone under fluoroscopic and ultrasound imaging guidance.

In some embodiments, the applying Histotripsy therapy steps comprise applying Histotripsy therapy with a multi-mode transducer. In other embodiments, the applying Lithotripsy therapy step comprises applying Lithotripsy therapy with the multi-mode transducer.

In one embodiment, the applying Histotripsy therapy steps comprise applying Histotripsy therapy at a first pulse repetition frequency, wherein the applying Lithotripsy therapy step comprises applying Lithotripsy therapy at a second pulse repetition frequency, the method further comprising interleaving Histotripsy therapy and Lithotripsy therapy with virtually no change in the first and second pulse repetition rates.

Another method of treating a target tissue is provided, comprising delivering a first Lithotripsy pulse to the target tissue, delivering a sequence of Histotripsy pulses to the target tissue after the first Lithotripsy pulse, and delivering a second Lithotripsy pulse to the target tissue after the sequence of Histotripsy pulses, wherein the first and second Lithotripsy pulses are separated in time by a pulse repetition frequency. In some embodiments, the target tissue is a urinary stone.

In some embodiments, the method further comprises delivering a sequence of Histotripsy pulses immediately prior to delivering the first Lithotripsy pulse to the target tissue to suppress cavitation. In additional embodiments, the method further comprises delivering a sequence of Histotripsy pulses immediately prior to delivering the second Lithotripsy pulse to the target tissue to suppress cavitation.

In some embodiments, the method further comprises delivering a spatially-varying cavitation suppressing Histotripsy field to allow cavitation to occur within the target tissue while suppressing cavitation outside the target tissue.

DETAILED DESCRIPTION OF THE INVENTION

In addition to imaging tissue, ultrasound technology is increasingly being used to treat and destroy tissue. In medical applications such as Histotripsy, ultrasound pulses are used to form cavitational microbubbles in tissue to mechanically break down and destroy tissue. In Lithotripsy procedures, ultrasound pulses are used to form acoustic shockwaves that break up urinary stones into smaller fragments. Particular challenges arise in using Lithotripsy to break up urinary stones, including failing to break stones down into sizes small and smooth enough to pass comfortably, as well as visualizing and tracking the stones within the patient. The present invention describes several embodiments of devices and methods for treating urinary stones or other calculi including, but not limited to biliary calculi such as gall stones, particularly through the combination of Histotripsy and Lithotripsy therapy in a single procedure.

Despite the difference between Lithotripsy and Histotripsy, the aperture size, focal characteristics, and piezoelectric materials of the relative transducers are similar in both types of therapy. Thus, a single transducer can be driven in both Histotripsy and Lithotripsy modes. This dual-mode Histotripsy and Lithotripsy system can be configured to treat, fractionate, and dissolve urinary stones in patients suffering from urinary stones.

In some embodiments, a multi-mode Lithotripsy-Histotripsy device is configured to shift virtually instantaneously (electronic speeds) from a Lithotripsy shock wave mode (L-mode) to the Histotripsy "soft" erosion mode (H-mode). The primary advantages of a dual mode Lithotripsy-Histotripsy system are: (1) ability to rapidly fractionate urinary stones into smaller gravel like fragments in L-mode, which can be reduced in size more quickly by H-mode erosion (erosion is effectively a surface phenomena) because of the greatly increased surface area of the Lithotripsy fragments; (2) easy image guidance and initial focal targeting by utilizing the Histotripsy bubble cloud.

Despite the differences between Lithotripsy and Histotripsy, the aperture size, focal characteristics, and piezoelectric materials of the transducers needed for each system are similar. The circuitry and generators required to drive these transducers can be configured to drive a single transducer in both H and L-modes, or alternatively, can be configured to drive separate H-mode and L-mode transducers.

Figure 1A:
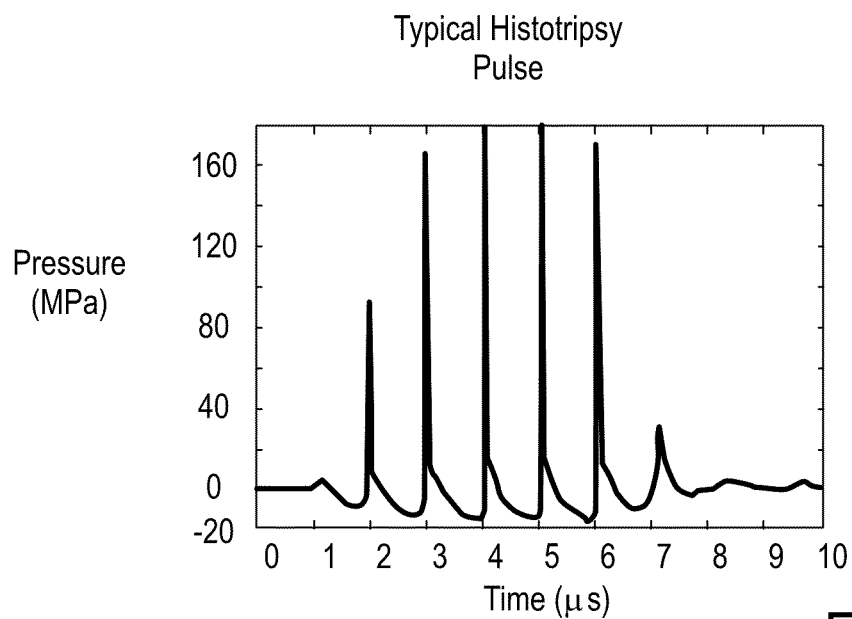
FIGS. 1A and 1B illustrate a typical Histotripsy pulse and Lithotripsy pulse, respectively.
Figure 1B:
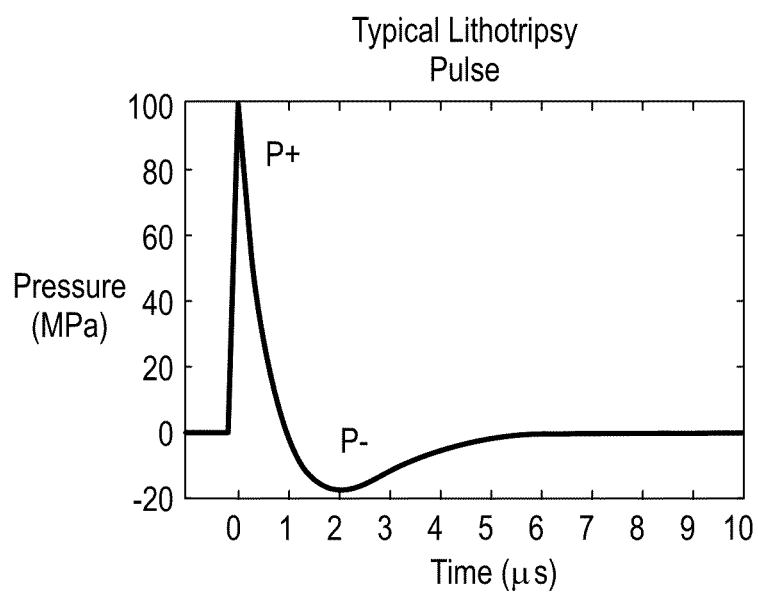
Figure 2A:
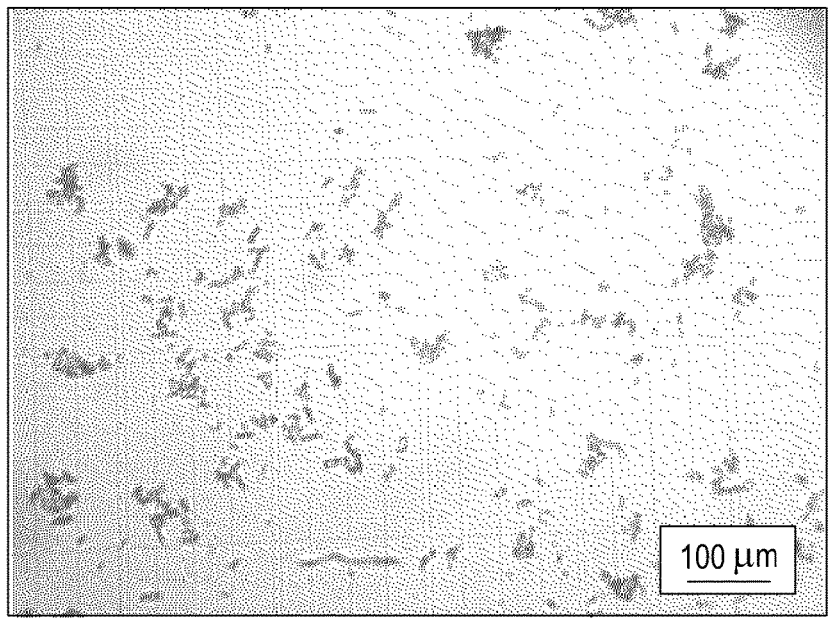
FIG. 2A illustrates a urinary stone eroded by Histotripsy therapy.
Figure 2B:
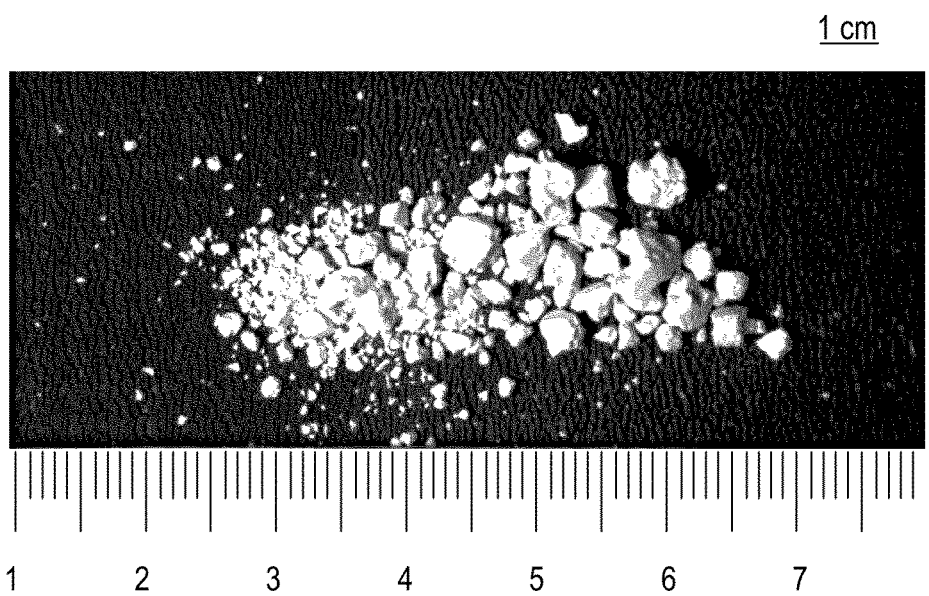
FIG. 2B illustrates a urinary stone fractionated by Lithotripsy therapy.
Figure 3:
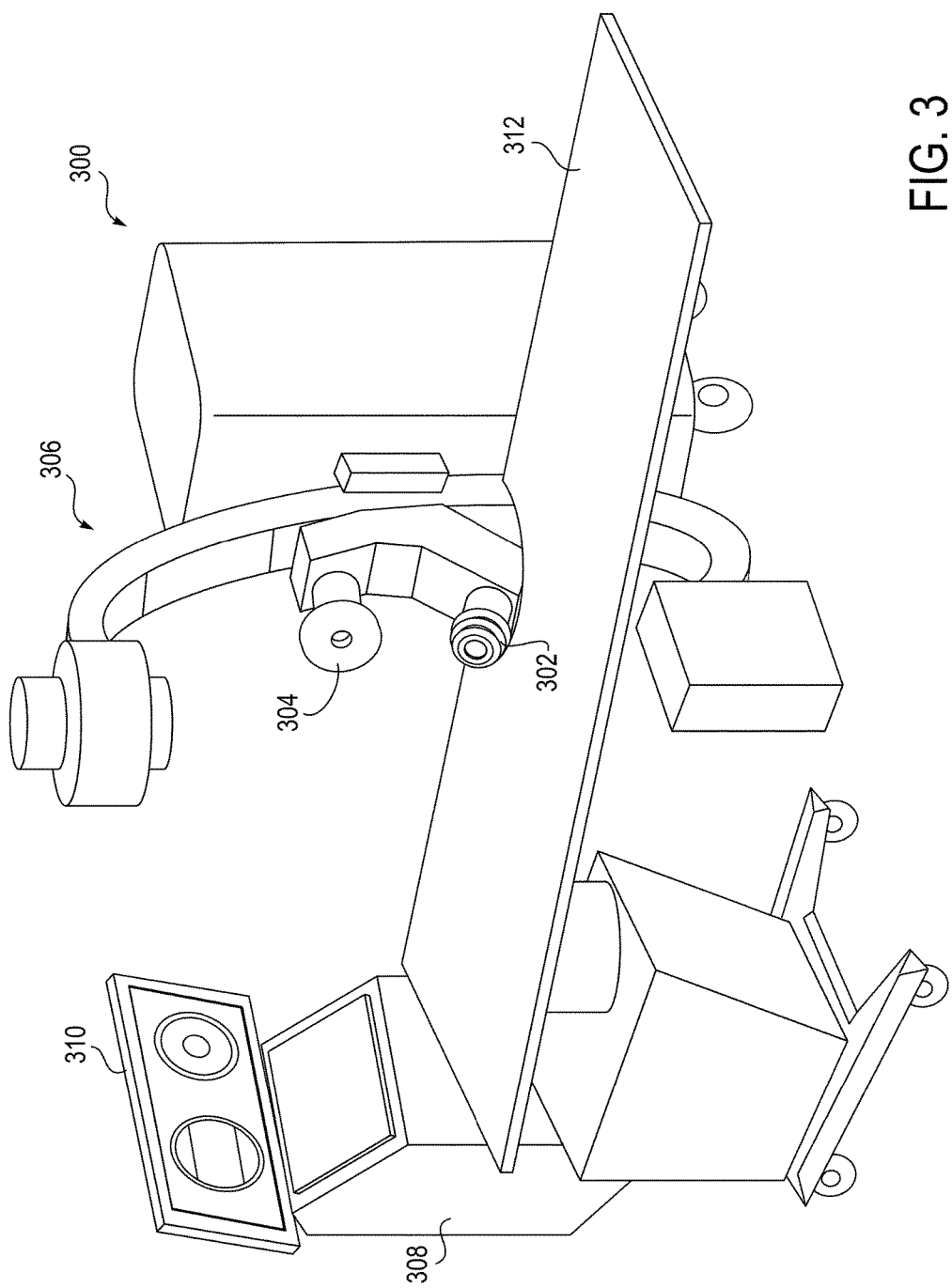
FIG. 3 illustrates one embodiment of a Lithotripsy-Histotripsy system.

FIG. 3 illustrates a combination Lithotripsy-Histotripsy system 300, comprising therapy transducer 302, therapy transducer 304, imaging system 306, control system 308, display 310, and patient support 312. In one embodiment, therapy transducer 302 can be a Lithotripsy transducer configured to operate in an L-mode to deliver Lithotripsy therapy to a target, and therapy transducer 304 can be a Histotripsy transducer configured to operate in an H-mode to deliver Histotripsy therapy to a target. In another embodiment, a combination Lithotripsy-Histotripsy system may include only a single transducer, such as therapy transducer 302, the transducer being configured to deliver both Lithotripsy therapy and Histotripsy therapy, without requiring a second therapy transducer 304. Therapy transducers 302 and 304 may have a single focus with mechanical or electromechanical steering of the respective Lithotripsy-Histotripsy focus. Alternatively, the therapy transducers may comprise a phased array to provide electrical steering of the focal point. Histotripsy transducers can be fabricated from piezo-electric ceramic materials that are pulsed with high voltage electric signals at ultrasonic frequencies. Lithotripsy transducers can be fabricated from piezo-electric ceramic materials or they may be magneto-resistive magnetic transducers or spark gap transducers, for example.

In some embodiments, Histotripsy transducers can apply acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle between approximately 0.1% and 5% and in some embodiments less than 5%, and a pulse repetition frequency of less than 5 KHz. In other embodiments, Lithotripsy transducers can apply acoustic pulses that operate at a frequency between approximately 50 KHz and 5 MHz, having a pulse intensity with a peak negative pressure of approximately 10-25 MPa, a peak positive pressure of more than 10 MPa, a pulse length of 1 cycle, a duty cycle less than 0.1%, and a pulse repetition frequency of less than 2 Hz.

Imaging system 306 can provide real-time imaging guidance of the patient while during L-mode and H-mode therapy. In the embodiment of FIG. 3, imaging system 306 comprises an ultrasound and fluoroscopic C-Arm imaging system. However, due to the size and cost of C-arm imaging solutions, in other embodiments the imaging system can comprise a high-resolution ultrasound imaging system. If an ultrasound imaging system is used, it can be separate from therapy transducers 302 and 304. Alternatively in some embodiments, the ultrasound imaging system can be disposed on or within the therapy transducers 302 and 304. Real-time imaging from imaging system 306 can be displayed on display 310, which can comprise and electronic display or a graphical user interface (GUI). In some embodiments, the display can visualize treatment from both the therapy transducers 302 and 304 at the same time, thus having the capability to overlap or fuse the fluoroscopic and ultrasonic images to optimize image planning and therapy tracking. Therapy transducers 302 and 304 and imaging system 306 can be packaged together as a single unit, as shown in FIG. 3, to facilitate imaging and treatment of a patient lying on patient support 312.

Control system 308 can include all the necessary drive electronics and signal generators necessary to drive therapy transducers 302 and 304 in both L-mode and H-mode. For example, the drive electronics and signal generators of control system 308 should be configured to drive therapy transducers 302 and/or 304 according to the parameters set forth in Table 1 above for both H-mode and L-mode transducers. The control system 308 can including a switching mechanism configured to instantaneously switch operation of the system between an L-mode and an H-mode, or to allow for simultaneous operation in H and L-modes. Control system 308 can further include a CPU or computer configured to set treatment parameters, receive and process imaging information, and direct L-mode and H-mode therapy according to a surgical plan. The therapy transducer drive electronics may be configured to generate both types of pulses as a pulse sequence in addition to Histotripsy pulses that optimize Lithotripsy pulses by suppressing and enhancing cavitation. One therapy transducer may have the capability of focusing outside of the target are to suppress cavitation and thereby provide active protection of tissues outside of the target area. This technique is more fully described in U.S. patent Ser. No. 12/121,001, filed May 15, 2008, titled "Pulsed Cavitational Ultrasound Therapy."

Figure 4:
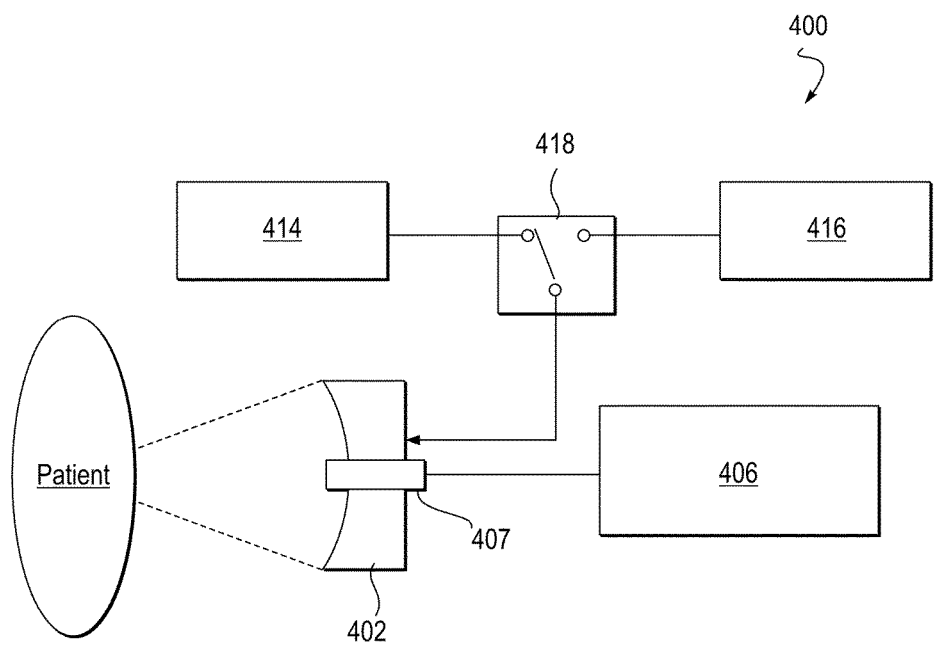
FIG. 4 illustrates a schematic view of a Lithotripsy-Histotripsy system.

FIG. 4 is a schematic drawing showing additional details of the system of FIG. 3. Lithotripsy-Histotripsy system 400 of FIG. 4 can include therapy transducer 402, imaging system 406, optional ultrasound imaging probe 407, H-mode driving system 414, L-mode driving system 416, and switching mechanism 418, which can be a physical or electronic control switch. In FIG. 4, therapy transducer 402 can represent either therapy transducers 302 and 304 of FIG. 3, or alternatively, can represent a single therapy transducer capable of both H and L-mode pulses. The Lithotripsy-Histotripsy system 400 of FIG. 4 allows virtually instantaneous switching between H-mode driving system 414 and the L-mode driving system 416 with electronic control switch 418 to allow an infinite range of possibilities for time division multiplexing of the H-mode and L-mode pulses.

Methods of using a Lithotripsy-Histotripsy system, such as the system described herein, will now be discussed. The choice of modality for treating patients with nephrolithiasis depends upon stone size, stone location, anatomic factors, patient factors, and patient preference. In general, for stones in the ureter or kidney having a size less than 2 cm in greatest dimension, shockwave Lithotripsy and ureteroscopy are first-line treatment options. For stones in the kidney (particularly those that reside in the lower pole of the kidney), percutaneous nephrolithotomy, albeit much more invasive of a procedure, can also be an appropriate option. Shockwave lithotripsy was the primary modality for managing these stones; however, advances in ureteroscopic instrumentation and technology have placed ureteroscopy on equal footing with shockwave lithotripsy, such that this has become the preferred first-line therapy at many academic medical centers.

The primary advantage of Histotripsy therapy over Lithotripsy therapy is the uniformly microscopic size of the reduced stone particles compared to Lithotripsy. For some stones which do not break down via L-mode therapy into sufficiently small fragments to be passed through the urinary tract, this may be critical. Some situations might be best approached primarily in the L-mode (harder stones in places where fragments are easily passed) and some situations might be best approached primarily in the H-mode (softer more easily eroded stones). Some may require a combination of each system with optimal application to be determined by clinical and laboratory experience with such a system. Additionally, visualization of Lithotripsy procedures is typically challenging and requires large and expensive imaging equipment, such as a fluoroscopic C-Arm. However, cavitational bubble clouds formed with a Histotripsy H-mode pulse can be easily viewed in real time under ultrasound imaging. Thus, it can be possible to visualize and target a urinary stone or by placing an H-mode bubble cloud on the stone, then focusing an L-mode shockwave towards the position of the bubble cloud to fragment the stone.

Thus, referring back to FIGS. 3-4, one method of treating urinary stones with a Lithotripsy-Histotripsy system (e.g., Lithotripsy-Histotripsy system 300/400 of FIG. 3/4) may include positioning a patient on a patient support (e.g., patient support 312 of FIG. 3) and imaging the patient with an imaging system (e.g., imaging system 306 of FIG. 3). The imaging system can be, for example, an ultrasound imaging system or a fluoroscopic imaging system. The method can include targeting a urinary stone or urinary stones within the patient with the imaging system. Next, the method can include focusing an H-mode therapy transducer (e.g., therapy transducer 304 of FIG. 3) on the urinary stone and generating a bubble cloud onto the stone under the ultrasound image guidance. The Histotripsy bubble cloud can be visualized as a greatly enhanced backscatter region on a visual display (e.g., display 310 of FIG. 3).

Next, the Lithotripsy-Histotripsy system can be switched to an L-mode with a switching mechanism (e.g., switching mechanism 418 of FIG. 4) to deliver a shock wave or shock waves to the urinary stone to macroscopically fractionate the stone. Verification of the focal position and its relationship to the urinary stone can be achieved by switching back to H-mode and visualizing the H-mode bubble cloud under imaging guidance. Furthermore, the H-mode bubble cloud can continue to erode the macroscopic urinary stone particles due to the increased surface area of multiple fractionated stone particles compared to the original urinary stone. The Histotripsy therapy can function to smooth (by erosion) the Lithotripsy fragments so as to facilitate passage of these fragments by removing sharp corners, edges, or elongated dimensions which can hinder passage of fragments through the ureter.

Thus, L-mode and H-modes of operation can be alternated so as to break down urinary stones into macroscopic particles (with L-mode pulses) and subsequently erode the macroscopic particles into a fine powder (with H-mode pulses). Histotripsy and Lithotripsy are naturally complementary as Lithotripsy shockwaves are efficient at causing initial coarse subdivision of targeted stones which greatly increases surface area and rate for subsequent Histotripsy erosion. Since the actual position of the original urinary stone can be tracked by image analysis (e.g., visual tracking of the stone itself or speckle tracking), the Lithotripsy-Histotripsy system can allow for movement of the kidney and can continually reposition the focus onto the tracked target volume. Visualization of the Histotripsy bubble cloud at the target position can confirm proper targeting.

In some method embodiments, urinary stones can be treated solely with Histotripsy H-mode pulses. Thus, Histotripsy acoustic sequences can be applied directly to the stones to cause erosion of the stones, producing extremely fine debris particles less than 100 μm in diameter which can be passed painlessly by the patient and eliminate the risk of steinstrasse (multiple obstructing fragments within the ureter). Still referring to FIGS. 3-4, another method of treating urinary stones with a Lithotripsy-Histotripsy system (e.g., Lithotripsy-Histotripsy system 300/400 of FIG. 3/4) may include positioning a patient on a patient support (e.g., patient support 312 of FIG. 3) and imaging the patient with an imaging system (e.g., imaging system 306 of FIG. 3). The method can further comprise targeting a urinary stone or urinary stones within the patient with the imaging system. Next, the method can include focusing an H-mode therapy transducer (e.g., therapy transducer 304 of FIG. 3) on the urinary stone and generating a bubble cloud onto the stone under the ultrasound image guidance. The Histotripsy bubble cloud can be visualized as a greatly enhanced backscatter region on a visual display (e.g., display 310 of FIG. 3). The method can further comprise applying Histotripsy therapy to the urinary stone to erode the stone into fine particles having a size less than 100 μm in diameter.

Figure 5:
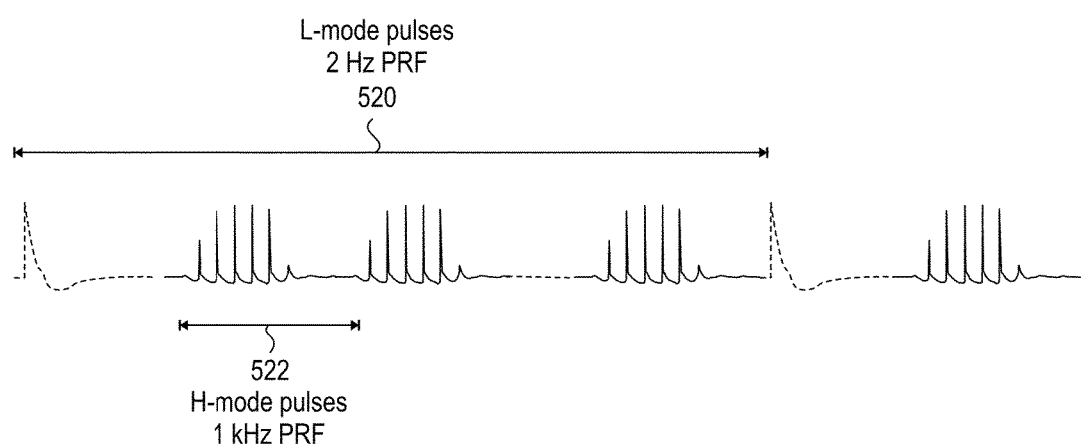
FIG. 5 illustrates a pulse sequence of Lithotripsy therapy interleaved with Histotripsy therapy.

Alternative embodiments of methods of treating urinary stones can include multi-frequency systems for additional optimization, e.g., L-mode at higher frequencies (probably about 1 MHz) to fragment the stone and H-mode at lower frequencies (about 500 Khz) to cover the whole stone area and to make sure the increased stone surface area is usable for enhanced surface-based erosion. Referring now to FIG. 5, since L-mode pulses 520 typically have a maximum pulse repetition frequency (PRF) about 2 Hz (2 pulses per second), and L-mode pulses are generally less than 100 microseconds long, most of the time during L-mode therapy is available for H-mode pulses 522. In some embodiments, L-mode pulses can have a maximum PRF of about 5 Hz. Since the H-mode PRF can be 1 kHz or larger, the H-mode pulses 522 and L-mode pulses 520 can progress together appropriately interleaved in time with little decrease in PRF for either, as shown in FIG. 5. Thus during urinary stone treatment, L-mode pulses can fracture a large urinary stone into fragments to increase the stone surface area for the H-mode, which can then progress virtually undiminished in PRF by temporal sharing with the L-mode. It should be noted that the H-mode can trap fragments within its focal field. This may allow trapping of L-mode fragments until the H-mode pulses erode all fragments to very small particles that then escape the trapping field.

This L-mode and H-mode interleaving technique can be used to treat urinary stones. Thus, referring back to FIGS. 3-5, one method of treating urinary stones with a Lithotripsy-Histotripsy system (e.g., Lithotripsy-Histotripsy system 300/400 of FIG. 3/4) may include positioning a patient on a patient support (e.g., patient support 312 of FIG. 3) and imaging the patient with an imaging system (e.g., imaging system 306 of FIG. 3). The imaging system can be, for example, an ultrasound imaging system or a fluoroscopic imaging system. The method can include targeting a urinary stone or urinary stones within the patient with the imaging system. Next, the method can include focusing an H-mode therapy transducer (e.g., therapy transducer 304 of FIG. 3) on the urinary stone and generating a bubble cloud onto the stone under the ultrasound image guidance. The Histotripsy bubble cloud can be visualized under ultrasound image guidance as a greatly enhanced backscatter region on a visual display (e.g., display 310 of FIG. 3). Since the bubble cloud cannot be imaged under solely fluoroscopic imaging, if no ultrasound imaging is used then the stones can be targeted by positioning the geometric focus of the therapy transducer (e.g., the expected location of the bubble cloud) on the targeted urinary stone.

Next, the Lithotripsy-Histotripsy system can generate an L-mode pulse to deliver a shock wave to the urinary stone to macroscopically fractionate the stone. Since L-mode pulses typically have a PRF≤2 Hz (but possibly ≤5 Hz), the time between subsequent L-mode pulses can be used to apply H-mode pulses, which typically have a PRF≤5 kHz. Thus, the method of treatment can comprise delivering an L-mode pulse to a urinary stone to fractionate the stone, instantaneously switching to an H-mode of operation to deliver a series of H-mode pulses to the urinary stone, and instantaneously switching back to an L-mode to deliver another Lithotripsy shockwave to the stone(s). As described above, verification of the stone position can be achieved by switching to H-mode and visualizing the H-mode bubble cloud under imaging guidance.

Histotripsy can be used to enhance shockwave (Lithotripsy) fragmentation of stones through control of the cavitation environment. Histotripsy can be used to control the cavitation environment to enhance and suppress cavitation at appropriate times. For example, Histotripsy can be used to suppress cavitation to improve efficacy at higher Lithotripsy shockwave rates. Additionally, Histotripsy can be used to suppress cavitation in healthy tissue to facilitate a higher Lithotripsy shockwave rate. High repetition rate Lithotripsy (>2 Hz) is currently limited by the persistence of microbubbles created during the process (cavitation) which interfere with subsequent shockwaves. Simple suppression of cavitation does not improve overall comminution because some cavitation is necessary for complete fragmentation. Time-varying Histotripsy sequences applied immediately before the arrival of a Lithotripsy shockwave to suppress cavitation, followed by enhancement sequences during the tensile portion of the Lithotripter wave (acting as a pump) can maximize both methods of comminution. This technique can greatly increase the efficiency of shockwaves as well as the rate which can be used allowing more complete comminution of even difficult urinary stones.

Cavitation suppressing Histotripsy acoustic sequences can be used to reduce collateral tissue injury during high dose and high rate shockwave application. Studies have shown increased risk of injury when high shockwave rates or high shockwave doses are attempted limiting the thoroughness and effectiveness of a treatment. A spatially-varying cavitation suppressing Histotripsy field can allow cavitation to occur within a target zone while suppressing cavitation outside the target zone. This technique can be used to eliminate collateral injury from shockwaves while permitting necessary cavitation on the stone surface when large shockwave doses and higher rates are used for more complete comminution. Thus, a method of treating tissue can comprise delivering Lithotripsy therapy to a target tissue to treat the target tissue, and delivering spatially-varying Histotripsy therapy to allow cavitation to occur within the target tissue while suppressing cavitation outside the target tissue.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:
1. A method of treating urinary stones, comprising:
applying Histotripsy therapy by transmitting Histotripsy ultrasound pulses having a pulse repetition frequency between 100 Hz and 1,000 Hz to generate a bubble cloud;
positioning the bubble cloud on a urinary stone;

applying Lithotripsy therapy by transmitting a Lithotripsy ultrasound pulse having a pulse repetition frequency less than or equal to 2 Hz to generate a shock wave to fractionate the urinary stone into macroscopic urinary stone particles;

applying the Histotripsy therapy to the macroscopic urinary stone particles to erode the macroscopic urinary stone particles; and displaying real-time imaging of treatment from the Histotripsy therapy and the Lithotripsy therapy on a display.

2. The method of claim 1 wherein the positioning step further comprises positioning the bubble cloud on the urinary stone under imaging guidance.

3. The method of claim 1 wherein the positioning step further comprises positioning the bubble cloud on the urinary stone under ultrasound imaging guidance.

4. The method of claim 1 wherein the positioning step further comprises positioning the bubble cloud on the urinary stone under fluoroscopic and ultrasound imaging guidance.

5. The method of claim 1 wherein the applying Histotripsy therapy steps comprise applying Histotripsy therapy with a multi-mode transducer.

6. The method of claim 5 wherein the applying Lithotripsy therapy step comprises applying Lithotripsy therapy with the multi-mode transducer.

7. The method of claim 1 wherein the applying Histotripsy therapy steps comprise applying Histotripsy therapy at a first pulse repetition frequency, wherein the applying Lithotripsy therapy step comprises applying Lithotripsy therapy at a second pulse repetition frequency, the method further comprising interleaving Histotripsy therapy and Lithotripsy therapy with virtually no change in the first and second pulse repetition rates.

8. A method of treating a target tissue, comprising:
delivering a first Lithotripsy pulse to the target tissue;
delivering a sequence of Histotripsy pulses having a pulse repetition frequency between 100 Hz and 1,000 Hz to the target tissue after the first Lithotripsy pulse;
delivering a second Lithotripsy pulse to the target tissue after the sequence of Histotripsy pulses, wherein the first and second Lithotripsy pulses are separated in time by a pulse repetition frequency less than or equal to 2 Hz; and
displaying real-time imaging of treatment from the Histotripsy pulses and the first and second Lithotripsy pulses on a display.

9. The method of claim 8 wherein the target tissue is a urinary stone.

10. The method of claim 8 further comprising, prior to delivering the first Lithotripsy pulse to the target tissue, delivering a sequence of Histotripsy pulses to suppress cavitation.

11. The method of claim 10 further comprising, prior to delivering the second Lithotripsy pulse to the target tissue, delivering a sequence of Histotripsy pulses to suppress cavitation.

12. The method of claim 8 further comprising delivering a cavitation suppressing Histotripsy field to allow cavitation to occur within the target tissue while suppressing cavitation outside the target tissue.

* * * * *